United States Patent [19]

Gilomen

[11] Patent Number: 4,850,987
[45] Date of Patent: Jul. 25, 1989

[54] WASHABLE DIAPER PANTIES

[76] Inventor: Esther Gilomen, Bartenheimerstrasse 13, CH-4005 Basel, Switzerland

[21] Appl. No.: 129,377

[22] Filed: Nov. 24, 1987

Related U.S. Application Data

[63] Continuation of Ser. No. 844,170, Mar. 28, 1986, abandoned.

[51] Int. Cl.$^4$ .............................................. A61F 13/16
[52] U.S. Cl. ................................ 604/385.1; 604/393; 604/377
[58] Field of Search ............... 604/391, 393, 377, 397, 604/398, 385 A, 385 R, 394

[56] References Cited

U.S. PATENT DOCUMENTS

| | | | |
|---|---|---|---|
| 1,989,283 | 1/1935 | Limacher | 604/385.1 |
| 2,532,029 | 11/1950 | Medoff | 604/397 |
| 2,577,398 | 12/1951 | Blake | 604/394 |
| 2,684,677 | 7/1954 | Pinney | 604/385.1 |
| 2,898,912 | 8/1959 | Adams | 604/397 |
| 3,171,773 | 3/1965 | Estes et al. | 604/397 |
| 3,955,575 | 5/1976 | Okuda | 604/391 |
| 3,968,798 | 7/1976 | Hokanson | 604/397 |
| 4,182,334 | 1/1980 | Johnson | 604/393 |
| 4,244,367 | 1/1981 | Rollenhagen | 604/397 |
| 4,300,563 | 11/1981 | Brookfield | 604/377 |
| 4,360,022 | 11/1982 | Usami et al. | 604/377 |
| 4,363,322 | 12/1982 | Andersson | 604/377 |
| 4,573,990 | 3/1986 | Ohsaki | 604/385 R |
| 4,676,787 | 6/1987 | Sergeant | 604/385 A |

FOREIGN PATENT DOCUMENTS

| | | |
|---|---|---|
| 814881 | 7/1949 | Fed. Rep. of Germany . |
| 1070779 | 12/1959 | Fed. Rep. of Germany . |
| 1870801 | 1/1963 | Fed. Rep. of Germany . |
| 1883811 | 12/1963 | Fed. Rep. of Germany . |
| 1884904 | 12/1963 | Fed. Rep. of Germany . |
| 2206282 | 8/1973 | Fed. Rep. of Germany . |
| 7414275 | 4/1974 | Fed. Rep. of Germany . |
| 2532111 | 2/1976 | Fed. Rep. of Germany . |
| 2731911 | 2/1979 | Fed. Rep. of Germany . |
| 3317117 | 6/1984 | Fed. Rep. of Germany . |
| 7503278 | 11/1976 | France . |
| 673984 | 6/1952 | United Kingdom . |
| 2083778 | 3/1982 | United Kingdom ............... 604/377 |

Primary Examiner—C. Fred Rosenbaum
Assistant Examiner—Denise Whelton
Attorney, Agent, or Firm—Ralph W. Selitto, Jr.

[57] ABSTRACT

A diaper panty is made of a rectangular basic body of cotton and rectangular liner sewn to an upper edge zone thereof. Consequently, the liner can be lifted off from the basic body to the seam to make it possible to place a loose, absorbent insert between the liner and the basic body.

8 Claims, 1 Drawing Sheet

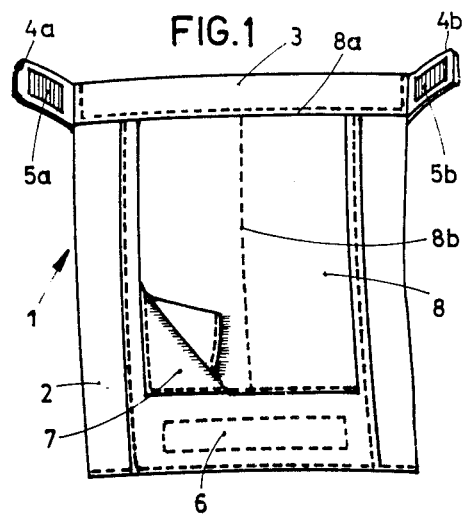
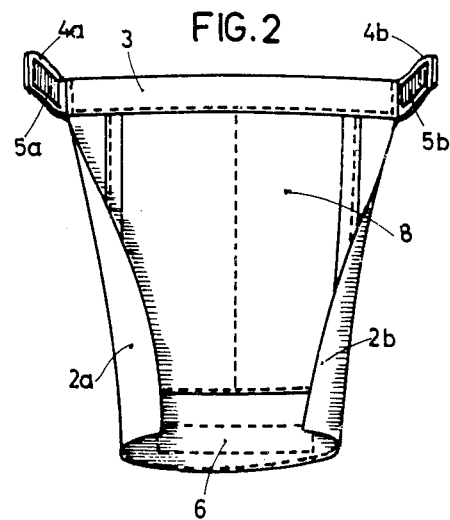
FIG.1 FIG.2
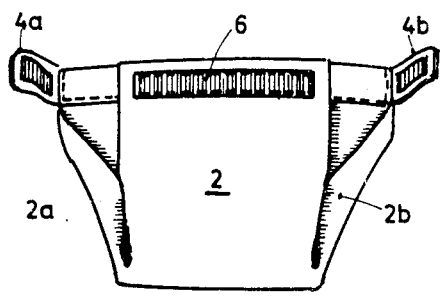
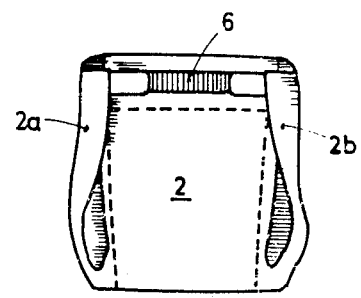
FIG. 3 FIG. 4
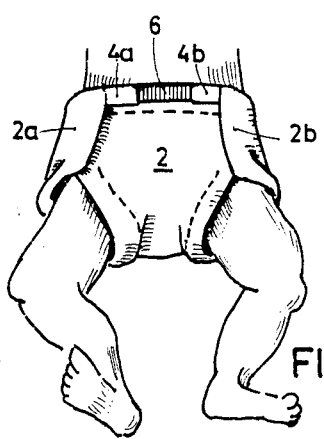
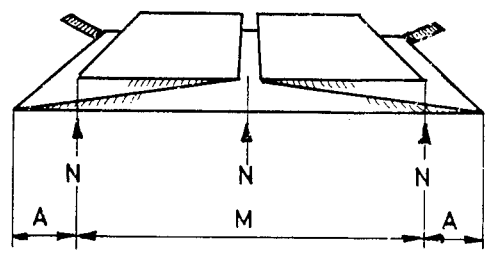
FIG. 5 FIG. 6

WASHABLE DIAPER PANTIES

This is a continuation of application Ser. No. 844,170, filed Mar. 28, 1986, now abandoned.

The invention relates to a washable diaper. In an ideal case, washable diaper panties would have great absorbency, be adapted to be put on quickly and in a simple way, and have to fit an infant's body so that, on the one hand, they would fit without moving out of position and, on the other hand, they would not be too tight to the body in any place.

A generally known cloth diaper consists of a rectangular cotton cloth which is multi-folded and fastened together after being put on. Since it is a necessity to change diapers on an infant, often the time-consuming folding is disadvantageous; furthermore, the manner of fastening this simple diaper shape leaves much to be desired with regard to moving out of position and avoiding pressure spots.

Further known in the art are, for example, diaper panties (Swiss Pat. No. 497,895) which have a strip of elastic material adjustable according to the width of the abdomen, the strip having eyes which cooperates with hooks fastened on the side of the diaper panties. However, such elastic tension parts exert, if they are to provide a tight fit, a constant pressure on the body of an infant, and attachment hooks and eyes should be avoided for reasons of safety and comfort.

Swiss Pat. No. 537,711 describes a baby diaper which consists of a plastic foil provided with a liquid-absorbing layer, the upper edge zone of the plastic foil being shaped into two tips which are to be pushed through holes disposed at both sides of the absorbent layer and tied together in a knot. Naturally, the absorption capacity of this plastic diaper is relatively low so that it can only be used for infants wetting but little. It also seals off air, easily leading to an undesired accumulation of heat, and the knot, which must be made in the area of an infant's abdomen, has a hindering effect when the infant lies on its stomach.

Thus, it is the object of the present invention to remove the deficiencies of the existing diaper panties with a washable, i.e. reusable, diaper panty made of cotton, which can be put on in a very simple manner without being folded, and which also permits, according to need, various degrees of liquid-absorption, a simple closure being easily adaptable to the stature of an infant without any risk of pressure spots, and the protection against wetness being fashioned according to the sensitiveness of an infant or according to the wish of the mother.

A practical example of the invention is hereinafter described by means of the attached drawing.

FIG. 1 is a simplified frontal view of the diaper panties.

FIGS. 2 to 4 show three different phases of putting on the diaper panties.

FIG. 5 shows the diaper panties already put on, and

FIG. 6 shows a method of producing the basic body.

According to FIG. 1, the diaper panties being designated with 1 show a substantially rectangular basic body 2, which is a single-layer or multi-layer cotton cloth. The upper edge zone 3, which is bent down toward the inside and reinforced in this way, extends to both sides in the form of two fastening flaps 4a/4b, each of which has a burying strap 5a/5b on the inside thereof.

A further burrying strip 6 is provided on the opposite side of the basic body 2, in the lower edge zone thereof.

A cloth overlay 7, which is also rectangular, is placed on the basic body in the middle section thereof and is sewn together with the basic body 2 on all sides in order to improve the absorbency of the latter in this area. In a preferred embodiment this cloth overlay is made of a cotton crepe.

A covering flap 8 is further sewn to the upper edge zone 3. This covering flap consists of a four-fold cotton fabric (a crepe); it can be bent off to the outside around the seam designated with 8a, i.e. it can be lifted off from the basic body 2. The seam 8b of covering flap 8 is preferably not made laterally, but in the center, in order to avoid an undesirable warpage when washing.

Due to covering flap 8 the absorbency in the middle area, which is especially exposed to liquid, is increased; on the other hand, one can place, if necessary, a loose absorbent insert between the covering flap 8 and the basic body 2; in this way skin contact will not occur with this, if need be, impregnated insert.

FIGS. 2 to 4 show how the described diaper panties are put on. When covering flap 8 with or without an insert has been bent down toward the inside (FIG. 1), both edge zones 2a and 2b according to FIG. 2 are first folded toward the inside in the form of a Z, or—if the stool of an infant is rather liquid—they are formed into a roll. Then the infant is laid on the diaper panties and the lower portion of the latter is folded upwards and fastened by means of burrying fasteners 4a/4b/6 according to FIG. 3. Due to this type of fastening, one can put on the diaper panties so satisfactorily that they do not move out of position, or are too tight to the body. A burrying fastener further permits a growth- or situation-related adaptation.

FIG. 6 illustrates a practical and useful way of manufacturing a cotton-made basic body 2. A rectangular cotton cloth is folded in the form of a Z on both sides so that the middle area M has three fabric layers, while both outer areas A have two fabric layers. A longitudinal seam is provided in each location designated with N. In this way the basic body 2 itself can absorb more liquid in the middle area than in both edge areas A.

It is a further advantage of the described diaper panties that due to being constructed as a basic body 2, a covering flap 8, and a loose insert, they dry fast after washing.

An indication of cotton in the present specification means that the cotton fabric used must contain at least 80% cotton.

In the diaper panties described one has deliberately renounced outer rubber-proofing or another protection against wetness because it only brings about disadvantages for an infant. Furthermore, special attention has been paid to that outer air is given access to the body of an infant. Insofar the diaper panties described also turn against the present trend to bundle the body of an infant as compact and airtight as possible. They also avoid blood circulation disorder, which are caused by rubber parts.

The rectangular form of the diaper panties, which has been chosen in conscious contrast with the cut-out form of known moisture-proof panties, brings with it a decisive advantage for the swaddling practice. On the one hand, it is possible in this way to fold the basic body 2, in a normal case, at both two-layer outer areas A (FIG. 6) either in a simple fashion, or—more advantageously—in the form of a Z. This provides a good leg-packing (sealing) at optimal airing and unrestrained comfort of movement.

Furthermore, because of the rectangular form of the basic body 2, the outer areas A have a sufficiently wide edge zone which, for example, can be rolled up in the case an infant has diarrhoea. By doing so there are formed sealing rolls on both sides which individually increase tightness in the leg area. This is achieved without having to compromise with regard to tolerance and air permeability, as this is the case in all prior art models.

I claim:

1. A reusable diaper, comprising a body made from a single piece of absorbent material and having a generally rectangular shape such that said body has a width, a length, a pair of generally parallel longitudinally-extending edges, a pair of generally parallel laterally-extending edges, an inner surface on one side of said body, an outer surface on an opposite side of said body, a first fold line extending parallel to one of said longitudinally-extending edges of said body and being spaced a first distance from said one longitudinally-extending edge of said body, a second fold line extending parallel to said one longitudinally-extending edge of said body and being spaced a second distance from said one longitudinally-extending edge of said body, said second distance being less than said first distance and said second fold line being positioned between said first fold line and said one longitudinally-extending edge of said body such that said first and second fold lines are separated by a third distance which is greater than said second distance, a third fold line extending parallel to the other of said longitudinally-extending edges of said body and being spaced a fourth distance from said other longitudinally-extending edge of said body, said third fold line cooperating with said first fold line to delimit a first panel of said body, a fourth fold line extending parallel to said other longitudinally-extending edge of said body and being spaced a fifth distance from said other longitudinally-extending edge of said body, said fifth distance being less than said fourth distance and said fourth fold line being positioned between said third fold line and said other longitudinally-extending edge of said body such that said third and fourth fold lines are separated by a sixth distance which is greater than said fifth distance, said body being folded along said first and second fold lines such that a second panel delimited by said first fold line and said second fold line covers a first portion of said first panel and a third panel delimited by said second fold line and said one longitudinally-extending edge of said body covers a portion of said second panel and said body being folded along said third and fourth fold lines such that a fourth panel delimited by said third fold line and said fourth fold line covers a second portion of said first panel and a fifth panel delimited by said fourth fold line and said other longitudinally-extending edge of said body covers a portion of said fourth panel, said first panel cooperating with said second, third, fourth and fifth panels to form a central zone which includes three layers of absorbent material, said first panel cooperating with said second panel to form a first marginal zone which is arranged alongside a first longitudinally-extending edge of said central zone and which includes two layers of absorbent material, and said first panel cooperating with said fourth panel to form a second marginal zone which is arranged alongside a second longitudinally-extending edge of said central zone and which includes two layers of absorbent material, each of said first and second marginal zones extending along substantially the entire length of said body and being foldable in a lateral direction and a longitudinal direction relative to said body for the purpose of forming seals which inhibit the escape of excrement when the diaper is applied to an infant in such a manner that said inner surface of said body comes into contact with the infant's skin and said laterally-extending edges of said body are attached to each other so as to encircle the infant's waist and so as to cause said first and second marginal zones of said body to encircle the infant's legs; a first seam formed along said second fold line; a second seam formed along said fourth fold line; a third seam formed along said one longitudinally-extending edge of said body; a fourth seam formed along said other longitudinally-extending edge of said body; a substantially flat liner made from absorbent material and having a generally rectangular shape such that said liner includes a pair of generally parallel longitudinally-extending edges and a pair of generally parallel laterally-extending edges, said liner having a width which is less than the width of said body and a length which is no greater than the length of said body; and attaching means for attaching one of said laterally-extending edges of said liner and said one laterally-extending edge only to said inner surface of said body proximate to one of said laterally-extending edges of said body such that the other of said laterally-extending edges of said liner is free and is generally parallel to the other of said laterally-extending edges of said body, one of said longitudinally-extending edges of said liner is free and is generally parallel to said first longitudinally-extending edge of said central zone of said body and the other of said longitudinally-extending edges of said liner is free and is generally parallel to said second longitudinally-extending edge of said central zone of said body, whereby said liner substantially covers said central zone but does not substantially cover said first and second marginal zones.

2. A reusable diaper according to claim 1, further comprising an absorbent overlay attached to said central zone of said body between said body and said liner, said overlay covering at least a portion of said central zone of said body.

3. A reusable diaper according to claim 2, wherein said body, said liner and said overlay are made from a cotton fabric.

4. A reusable diaper according to claim 3, wherein said liner and said overlay are made from a cotton crepe.

5. A reusable diaper according to claim 1, wherein said body and said liner cooperate to form receiving means for receiving an absorbent insert such that said insert is interposed between said body and said liner.

6. A reusable diaper according to claim 1, wherein said one laterally-extending edge of said body includes reinforcing means for reinforcing said one laterally-extending edge of said body.

7. A reusable diaper according to claim 6, wherein said reinforcing means is formed by folding said one laterally-extending edge of said body over onto itself.

8. A reusable diaper according to claim 6, further comprising first fastening means located on said outer surface of said body proximate to said other laterally-extending edge of said body, second fastening means extending laterally outward from said first marginal zone of said body in the vicinity of said one laterally extending edge of said body and third fastening means extending laterally outward from said second marginal zone of said body in the vicinity of said one laterally-extending edge of said body, said second and third fastening means being releaseably engageable with said first fastening means when the diaper is applied to an infant in such a manner that said liner and said inner surface of said body come into contact with the infant's skin and said laterally-extending edges of said body are attached to each other by said first, second and third fastening means so as to encircle the infant's waist and so as to cause said first and second marginal zones of said body to encircle the infant's legs.

* * * * *